United States Patent [19]

Rappoldt et al.

[11] Patent Number: 4,464,298
[45] Date of Patent: Aug. 7, 1984

[54] METHOD OF PREPARING Δ5,7-STEROIDS

[75] Inventors: Menso P. Rappoldt; Louis F. Pauli; Jan Hoogendoorn, all of Weesp, Netherlands

[73] Assignee: Duphar International Research B.V., Weesp, Netherlands

[21] Appl. No.: 457,191

[22] Filed: Jan. 11, 1983

[30] Foreign Application Priority Data

Jan. 14, 1982 [NL] Netherlands ............... 8200128

[51] Int. Cl.³ ............................................. C07J 17/00
[52] U.S. Cl. ..................... 260/239.55 C; 260/397.2; 260/397.4; 260/397.5
[58] Field of Search ............... 260/397.2, 397.4, 397.5, 260/239.55 C

[56] References Cited

U.S. PATENT DOCUMENTS 4,116,985 9/1978 Salmond .................... 260/397.2

FOREIGN PATENT DOCUMENTS 939100 10/1963 United Kingdom .......... 260/397.2

Primary Examiner—Elbert L. Roberts
Attorney, Agent, or Firm—Stevens, Davis, Miller & Mosher

[57] ABSTRACT

The invention relates to a method of preparing Δ5,7-steroids, in particular 7-dehydrocholesterol compounds, of the general formula:

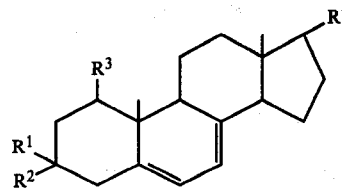

wherein
R is a hydrogen atom, a hydroxy group, optionally etherified with a $C_1$–$C_4$ alkanol or esterified with a $C_1$–$C_4$ alkane carboxylic acid, a $C_2$–$C_5$ alkanoyl group, optionally ketalized with a $C_1$–$C_4$ alkanol, or a branched or non-branched, saturated or unsaturated $C_1$–$C_{10}$ alkyl group, optionally substituted with one or more fluorine atoms or hydroxy groups, which hydroxygroup or groups is (are) optionally etherified with $C_1$–$C_4$ alkanol(s) or esterified with $C_1$–$C_4$ alkane carboxylic acid(s), and
$R^1$, $R^2$ and $R^3$ are equal or different and represent hydrogen atoms or hydroxy groups, optionally etherified with $C_1$–$C_4$ alkanols or esterified with $C_1$–$C_4$ alkane carboxylic acids, or wherein $R^1$ and $R^2$ together constitute a $C_2$–$C_4$ alkylene dioxy group, by dehydrobrominating 7-bromo-Δ5-steroids under the influence of a fluoride as a base in an organic solvent.

25 Claims, No Drawings

METHOD OF PREPARING Δ5,7-STEROIDS

The invention relates to a method of preparing Δ5,7-steroids, in particular 7-dehydrocholesterol compounds, of the general formula:

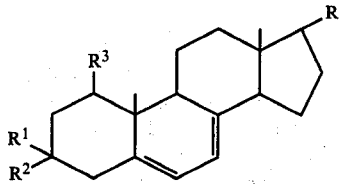

wherein
R is a hydrogen atom, a hydroxy group, optionally etherified with a $C_1$-$C_4$ alkanol or esterified with a $C_1$-$C_4$ alkane carboxylic acid, a $C_2$-$C_5$ alkanoyl group, optionally ketalized with a $C_1$-$C_4$ alkanol, or a branched or non-branched, saturated or unsaturated $C_1$-$C_{10}$ alkyl group, optionally substituted with one or more fluorine atoms or hydroxy group, which hydroxy group or groups is (are) optionally etherified with $C_1$-$C_4$ alkanol(s) or esterified with $C_1$-$C_4$ alkane carboxylic acid(s), and
$R^1$, $R^2$ and $R^3$ are equal or different and represent hydrogen atoms or hydroxy groups, optionally etherified with $C_1$-$C_4$ alkanols or esterified with $C_1$-$C_4$ alkane carboxylic acids, or wherein $R^1$ and $R^2$ together constitute a $C_2$-$C_4$ alkylene dioxy group,
by dehydrobrominating 7-bromo-Δ5-steroids under the influence of a base in an organic solvent.

It is generally known that many steroids and compounds derived from steroids have an interesting biological activity. For example, vitamin D compounds, for example, vitamin $D_3$ or hydroxylated vitamin $D_3$, may be used in all those cases in which problems with the calcium metabolism play a part. A good possibility of synthesizing these biologically active compounds from naturally occurring material is therefore of great importance and has been the subject matter of searchers for more than thirty years.

Important intermediate products in the preparation of these biologically active steroids or compounds derived from steroids are the Δ5,7-steroids. These 5,7-diene steroids are usually synthesized from compounds having a Δ5-steroid structure, which structure is present in many naturally occurring steroids. An example of such an abundantly naturally occurring Δ5-steroid is cholesterol. However, selective introduction of a double bond in the 7-position of a Δ5-steroid has presented problems to many searchers in this field. In this reaction, the first reaction step is the introduction of a bromine atom in the allylic place of the Δ5-steroid molecule, for example with N-bromo succinimide or dibromo-dimethylhydantoin; the desired 7-bromo-Δ5-steroid is formed in a high yield. In the subsequent dehydrobromination, however, usually two isomers are formed, namely the isomeric 4,6-diene in addition to the desired Δ5,7-steroid. Furthermore, trienes are often found in the reaction mixture as contaminations. For example, Hunziker and Müllner (Helv. Chim. Act. 41 (1958), 70) when using trimethyl phosphite as a dehydrobromination agent have obtained a product in a yield of 93% in which the desired 5,7-diene was present in a content of 55.8%. Other frequently used dehydrobromination agents are organic bases, for example, s-collidine; according to Hungarian Patent Specification No. 141005, under the influence of s-collidine a dehydrobromination product was obtained in a yield of 36%, which contained 51% of the desired 5,7-diene.

In German Patent Specification No. 1.154.466 1,3,2-dioxaphospholan is described as a dehydrobromination agent; in this case a product was obtained in a yield of 53-60% which consisted for 80-100% of the desired 5,7-diene. In a recent publication by Confalone c.s. in J. Org. Chem. 1981, 46, 1030-32 a new synthesis of 7-dehydrocholesterols is described in which the formation of the 4,6-diene isomer is avoided entirely. According to this method, the 7-bromocholesterol ester, after equilibration, is converted with benzene thiol into the corresponding phenyl sulphide, which substance, after oxidation with a peroxy acid to the sulphoxide, under the influence of triethyl amine as a base yields the desired 7-dehydrocholesterol ester without contamination with the 4,6-diene isomer in a yield of 53%. Although the last-mentioned dehydrobromination selectively leads to the desired 5,7-diene, the yield still is unsatisfactory and the roundabout way via sulphide and sulphoxide (two extra reaction steps) forms a disadvantage.

According to another method described in German Patent Application No. 2547199, the 7-bromo compound is first converted into the 7-selenide which is oxidized to the selenium oxide, after which the desired Δ5,7-steroid is formed while splitting off the selenium oxide. This method has the same disadvantages as the above-described method via the sulphoxide. Another synthesis, as described recently by Barner c.s. in Helvetica Chimica Acta 64, 915 (1981) occurs via a tosyl hydrazone at carbon atom 7. The hydrazone is prepared from the 7-keto compound, which latter compound is obtained by oxidation of a Δ5-steroid with a chromic acid complex. By treating the thus prepared tosyl hydrazone with a suitable base, for example lithium hydride, the desired Δ5,7-diene is obtained in the pure state. Although Δ4,6-diene is not formed in this method of preparing either, the great number of reaction steps and the complexity of the synthesis constitute a serious disadvantage.

It has now been found that in the dehydrobromination of 7-bromo-Δ5-steroids under the influence of a base Δ5,7-steroids can be obtained in a very pure state and in a surprisingly high yield when a fluoride is used as a base. Fluorides suitable for this purpose are alkali metal fluorides or alkaline earth metal fluorides and in particular tetra(hydrocarbyl)ammonium fluorides the hydrocarbyl groups of which each have from 1 to 15 carbon atoms; examples of suitable hydrocarbyl groups are alkyl groups having from 1 to 12 carbon atoms and benzyl groups.

If desired, an organic base, for example an amine, such as s-collidine, may be present in the reaction mixture as an acid binder.

It is known to use tetraalkyl ammonium fluorides for elimination reactions. For example, in an article by Feit c.s. in J. Am. Chem. Soc. 97, Apr. 30, 1975, 2477-81, elimination reactions of secondary alkyl bromides are described in which tetraalkyl ammonium fluorides, tetraalkyl ammonium bromides and potassium alkoxides have been investigated as bases. However, no indication can be found in literature from which the surprisingly high yield and selectivity found when tetraalkyl ammonium fluorides are used for the preparation of Δ5,7-steroids can be explained. On the contrary, from the above-mentioned examination by Feit c.s. it appears that a tetraalkyl ammonium fluoride and a tetra alkyl ammonium bromide differ only slightly from each other as regards selectivity and both give, for example, from 4-methyl-2-penyl bromide, a high yield of 4-methyl-2-pentene in addition to little of the isomeric 4-methyl-1-pentene. This is in complete contrast with what was found in the dehydrobromination of 7-bromo-Δ5-steroids. For example, the isomeric 4,6-diene was obtained from 7α-bromocholesterol acetate under the influence of tetrabutyl ammonium bromide in tetrahydrofuran in a yield of 93%, whereas the same bromide in the presence of tetrabutyl ammonium fluoride was converted quantitatively into the desired Δ5,7-steroid.

A tetraalkyl ammonium fluoride the alkyl groups of which each have from 1 to 6 carbon atoms is preferably used as a base because herewith the best results are obtained. Of these compounds, tetrabutyl ammonium fluoride has been found to be excellently suitable.

It has been found that the dehydrobromination reaction to the desired 5,7-diene isomer runs off particularly readily when the fluoride used is substantially entirely anhydrous, namely preferably comprises less than 2 grammolecules of water per grammolecule of fluoride. By using a tetra(hydrocarbyl)ammonium fluoride, the water content hereof can best be reduced by freeze-drying to the desired value; it has been found that tetra(hydrocarbyl)ammonium fluoride after freeze-drying gives the best results. The fluoride may be used as such or, for example, bound to an ion exchanging resin or to silica gel, or in the form of a complex with a crown ether or a cryptate. In the former case, so when the fluoride as such is used, the best results are obtained.

The dehydrobromination reaction is preferably carried out under the influence of a fluoride in an aprotic solvent, preferably a solvent selected from the group consisting of tetrahydrofuran, toluene, dimethylformamide, acetone, a mixture of two of these solvents and a mixture of one of these solvents with an alkane having from 6 to 8 carbon atoms. The best results are obtained when tetrahydrofuran or a mixture of tetrahydrofuran and hexane or heptane is used as a solvent.

The temperature at which the dehydrobromination reaction is carried out is not particularly critical and is usually between $-10°$ C. and $120°$ C., dependent on the boiling-point of the solvent used. When the dehydrobromination reaction is carried out in tetrahydrofuran or in a mixture of tetrahydrofuran and hexane or heptane as a solvent, a reaction temperature is preferably chosen between $20°$ C. and $70°$ C.; most favourable is a temperature of approximately $25°$ C.

It has been found that the stereochemical purity of the starting material, i.c. the 7-bromo-Δ5-steroid, is a factor in the selective dehydrobromination. Pure crystalline 7α-bromo-Δ5-steroid gives the best yield of pure Δ5,7-diene isomer; in this case a yield of 100% can be reached with a quantitative conversion. In the above-mentioned allylic bromination of Δ5-steroids, technical 7-bromo-Δ5-steroids are obtained which consist of β-epimers for a considerable part, for example for 40 to 50%. In this mixture, the C7-epimers can be distinguished from each other by NMR-spectroscopy or by their respective 7α- and 7β-phenylsulphides, as described in the above-mentioned article by Confalone c.s. It is known from the same article by Confalone c.s. that the content of 7α-epimer in the C7-epimer mixture can be increased by causing the mixture to equilibrate in conditions suitable for that purpose, for example, by means of an excess of lithium bromide. It has now been found, however, that the desired epimerisation also takes place already in the presence of a considerably smaller quantity of bromide ions, for example, in the form of an alkali metal bromide, alkaline earth metal bromide or ammonium bromide, preferably a tetraalkyl ammonium bromide. Under circumstances suitable for this purpose, namely a reaction temperature of preferably approximately $0°-30°$ C. and in an aprotic solvent, preferably the same solvent in which the dehydrobromination is carried out, a mixture in which the α-epimer is present for at least 85% is obtained within a few hours from a technical mixture of 7α- and 7β-epimers, in the presence of 0.1 to 5 mol.%, preferably approximately 1 mol.% of bromide calculated on the mixture of epimers. When this mixture is used as the starting material in the dehydrobromination reaction, the desired Δ5,7-steroid is formed in a good selectivity. If desired, the 7α-epimer can be isolated pure and in the crystalline state by crystallization from a suitable organic solvent, preferably from acetone. When stored in a solvent, for example, tetrahydrofuran, the pure 7α-epimer thus obtained starts to epimerize, in which in the equilibrium condition approximately 8% β-epimer is present.

The invention will now be described in greater detail with reference to the ensuing specific examples.

EXAMPLE I (a) Preparation of pure 7α-bromocholesterol acetate 16.3 g of dibromodimethylhydantoin were added to a solution of 42.8 g of cholesterol acetate in 300 ml of petroleum ether ($40°-60°$ C.). The reaction mixture was refluxed for 1 hour while stirring thoroughly. After cooling, the solid (dimethylhydantoin) was filtered off; the solvent was distilled off from the filtrate under reduced pressure. In order to remove the last traces of solvent, 100 ml of acetone were added, after which the solution was again evaporated under reduced pressure. The residue was recrystallized from 50 ml of acetone; the α-epimer crystallized out at $0°$ C. After three recrystallizations from acetone, 12.6 g of pure 7α-bromocholesterol acetate were obtained having a melting-point of $113.9°-115.6°$ C.; according to the bromine content and the NMR spectrum, the substance was 100% pure.

(b) Preparation of 7-dehydro-cholesterol acetate 507.6 mg of the pure 7α-bromocholester acetate obtained sub (a) were dissolved in 5 ml of anhydrous tetrahydrofuran. To this solution was added at $25°$ C. a solution of 1.0 g of tetrabutyl ammonium fluoride which contained per mol 1 mol of crystal water, in 5 ml of anhydrous tetrahydrofuran, and then, after stirring at $20°-25°$ C. for 60 minutes, 10 ml of petroleum ether ($40°-60°$ C.). The 1 mole crystal water-containing tetrabutyl ammonium fluoride was obtained by freeze-drying a 10% solution in water. After washing the reaction mixture three times with 10 ml of water, the organic layer was evaporated to dryness. 426 mg (100%) of dry substance were obtained with a content of 7-dehydrocholesterol acetate of 100% (UV). The final product could be recrystallized from ethanol in which 400 mg of white crystalline material were obtained with a melting-point of $128°-129°$ C. The crystalline final product was 100% pure Δ5,7-cholestadienol acetate both according to the UV-absorption spectrum and according to the NMR spectrum.

In a corresponding manner, in which, if desired, 250 mg of s-collidine were added as an acid binder, the experiments recorded diagrammatically in the Table below were carried out to obtain 7-dehydrocholesterol acetate. The fluoride used, however, was dried in a vacuum, unless otherwise stated in the Table. In this Table, Bu$_4$NF, Et$_4$NF, THF and DMF mean tetrabutyl ammonium fluoride, tetraethyl ammonium fluoride, tetrahydrofuran and dimethyl formamide, respectively.

TABLE

| fluoride | solvent | reaction time (hours) | temp. (°C.) | conversion | yield % Δ 5,7 | % Δ 4,6 | remarks |
|---|---|---|---|---|---|---|---|
| KF | THF | 72 | 70 | 96 | 80 | 16 | |
| CsF | THF | 16 | 70 | 100 | 64 | 13 | |
| LiF | THF | 90 | 70 | 90 | 73 | 17 | |
| Et$_4$NF.2H$_2$O | THF | 16 | 70 | 100 | 73 | — | |
| Bu$_4$NF.2H$_2$O | THF | 0.3 | 70 | 100 | 90 | — | |
| Bu$_4$NF.H$_2$O | THF | 0.3 | 70 | 100 | 100 | — | * |
| Bu$_4$NF.H$_2$O | DMF | 2 | 25 | 100 | 96 | — | * |
| Bu$_4$NF.H$_2$O | toluene | 1.5 | 25 | 100 | 97 | — | * |
| Bu$_4$NF.H$_2$O | acetone | 3.5 | 25 | 100 | 66 | 2 | * |
| Bu$_4$NF.2H$_2$O | THF/hexane | 16 | 25 | 100 | 82 | — | ** |
| Bu$_4$NF.3H$_2$O | THF/hexane | 3 | 70 | 100 | 67 | — | ** |
| Bu$_4$NF/silica gel | THF | 1 | 70 | 100 | 78 | 2 | |
| F$^-$ resin | THF | 40 | 70 | 92 | 53 | 6 | *** |

Remarks:
*freeze-dried fluoride
**THF/hexane in a volume ratio of 1:1
***F$^-$ - resin is Amberlyst A-26F

EXAMPLE II

Preparation of 7-dehydrocholesterol acetate from cholesterol acetate, technical quality A mixture of 2.14 g of cholesterol acetate, technical quality, having a content of 96.2% and 0.81 g of di-bromo-dimethyl hydantoin in 75 ml of petroleum ether (40°–60° C.) was refluxed in a nitrogen atmosphere for 1 hour while stirring. After cooling and filtering the reaction mixture, the solvent was distilled off from the resulting filtrate under reduced pressure at a temperature below 25° C.; the residue was then dissolved in 20 ml of tetrahydrofuran. An amount of 13 mg tetrabutyl ammonium bromide were added to this solution, after which the reaction mixture was stirred at 20° C. for 50 minutes.

An amount of 4.9 g of freeze-dried tetrabutyl ammonium fluoride containing per mole 1 mole of crystal water dissolved in 25 ml of tetrahydrofuran was then added. The resulting reaction mixture was stirred at 10°–25° C. for 60 minutes and then taken up into 50 ml of petroleum ether (40°–60° C.). The resulting solution was washed three times with 50 ml of water. After evaporation to dryness of the organic phase, the residue was chromatographed over 150 g of silica gel with dichloromethane as the eluent. The fractions comprising the main components were combined and evaporated to dryness; 1,5 g of crude 7-dehydrocholesterol acetate were obtained. One crystallization from ethanol yielded 1.26 g of white crystalline final product having a content of 100% (UV and NMR) and a melting-point of 128°–129° C., which is a yield of 61%.

In a corresponding manner, Δ5,7-cholestadienol benzoate was obtained from cholesterol benzoate, technical quality, with a purity of 90% in a yield of 67%.

EXAMPLE III

Preparation of 25-hydroxy-7-dehydrocholesterol acetate

A mixture of 4.44 g of 25-hydroxycholesterol acetate with a purity of 97% and 3.56 g of dibromo-dimethyl hydantoin in 45 ml of cyclohexane was refluxed for 45 minutes in a nitrogen atmosphere. After cooling and filtering of the reaction mixture, the solvent was distilled off from the resulting filtrate under reduced pressure at a temperature below 25° C.; the residue was then dissolved in 45 ml of tetrahydrofuran. 32.2 mg of tetrabutyl ammonium bromide were added to this solution, after which the reaction mixture was stirred at 20° C. for 50 minutes. A solution of 9.8 g of freeze-dried tetrabutyl ammonium fluoride, containing per mole 1 mole of crystal water, in 41 ml of tetrahyrofuran was then added.

The reaction mixture was stirred at 20°–25° C. for 60 minutes and then taken up into 70 ml of a mixture of solvents of dichloromethane and hexane in a volume ratio of 2:3. The resulting solution was washed three times with 50 ml of water. After evaporating the organic phase to dryness, the residue was dissolved in 40 ml of ethyl acetate. While stirring carefully at −25° C. for 3 hours, the desired product crystallized out as a white crystalline substance having a melting-point of 137°–139.5° C.; yield 2.78 g (63.5). According to the UV-spectrum the purity was 98.3%.

EXAMPLE IV

Preparation of pregna-5,7-diene-3,20-dione-diethylene ketal

A mixture of 4.02 g of progesteronediketal, 5.75 ml of dichloromethane, 0.3 ml of s-collidine and 65 ml of n-hexane was heated to boiling while stirring. 1.61 g of dibromo-dimethyl hydantoin in 2.9 ml of dichloromethane were then added to this mixture in 10 minutes, after which the reaction mixture was stirred for another 2 minutes. After rapid cooling to 25° C., 23 ml of dichloromethane were added to the reaction mixture. After filtering, the solvent was distilled off from the resulting filtrate under reduced pressure. The residue was then dissolved in 50 ml of tetrahydrofuran.

40 mg of lithium bromide were added to this solution, after which the reaction mixture was stirred at 20° C. for 75 minutes.

A solution of 9.8 g of freeze-dried tetrabutyl ammonium fluoride, containing per mole 1 mole of crystal water, in 40 ml of tetrahydrofuran was then added. The reaction mixture was stirred at 20°–25° C. for 120 minutes and was then poured out into 50 ml of dichloromethane. The resulting solution was washed two times with 50 ml of water. After evaporating the organic phase to dryness, the residue was treated with 10 ml of boiling acetone. The desired pregna-5,7-diene-3,20-dione-diethylene ketal was obtained as a pale yellow crystalline substance in a yield of 3.02 g; according to the UV-spectrum the purity was 90%, so that the yield was 67.5%. The material could be obtained pure (UV) by a recrystallization from 9 ml of toluene; melting-point 185°–187° C.

EXAMPLE V

Preparation of cholesta-5,7-diene-3β,24R,25-triol-3-benzoate, 24-acetate 3.2 g of dibromodimethyl hydantoin were added to a solution of 10.4 g of cholest-5-ene-3β,24R,25-triol-3-benzoate,24-acetate in 20 ml of methylene chloride and 85 ml of cyclohexane. The mixture was then refluxed for 1 hour (50°) in a nitrogen atmosphere. After cooling the reaction mixture to 0° C., 28 ml of 0.5N NaOH solution were added while stirring. After separating the layers, the organic layer was washed with water till neutral and dried on $Na_2SO_4$.

After evaporating the solvent, the residue was taken up into 90 ml of anhydrous tetrahydrofuran. After adding 67 mg of tetrabutyl ammonium bromide, the mixture was stirred in a nitrogen atmosphere at room temperature for 1 hour. A solution of 20 g of freeze-dried tetrabutyl ammonium fluoride in 85 ml of dry tetrahydrofuran was added to this reaction mixture. After stirring at room temperature for 1 hour, the mixture was poured out on water/ice/ether. The layers were separated and the organic layer was washed with water till neutral. The collected water layers were once re-extracted with ether. The total organic layer was dried over $Na_2SO_4$. After evaporating the solvent, the residue (11.9 g) was chromatographed over 320 g of silica gel and eluted with methylene chloride-acetone mixtures increasing from 0 to 5%.

After combining the desired fractions and evaporating the solvent, 7.2 g of cholesta-5,7-diene-3β,24R,25-triol-3-benzoate, 24-acetate were obtained with a purity of 76.5%, so that the yield was 53%.

We claim:

1. A method of preparing Δ5,7-steroids, in particular 7-dehydrocholesterol compounds, of the general formula:

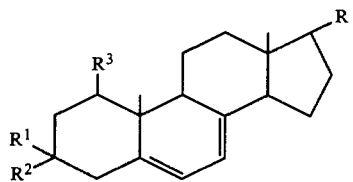

wherein
R is selected from the group consisting of a hydrogen atom, a hydroxy group selected from the group consisting of a free hydroxy group, an etherified hydroxy group with a $C_1$–$C_4$ alkanol, and an esterified hydroxy group with a $C_1$–$C_4$ alkane carboxylic acid, a $C_2$–$C_5$ alkanoyl group, and a $C_1$–$C_{10}$ aliphatic hydrocarbyl group, and $R^1$, $R^2$ and $R^3$ are equal or different and are selected from the group consisting of hydrogen atoms, hydroxy groups, and a $C_2$–$C_4$ alkylene dioxy group, by dehydrobrominating 7-bromo-Δ5-steroids under the influence of a base in an organic solvent, characterized in that a fluoride is used as a base, said fluoride being selected from the group consisting of an alkali metal fluoride, an alkaline earth metal fluoride, and a tetra(hydrocarbyl)ammonium fluoride, the hydrocarbyl groups of which each comprise from 1 to 15 carbon atoms.

2. A method as claimed in claim 1, characterized in that a tetraalkyl ammonium fluoride the alkyl groups of which each comprise from 1 to 6 carbon atoms, preferably tetrabutyl ammonium fluoride, is used as a base.

3. A method as claimed in claim 1, characterized in that a fluoride which comprises less than 2 grammolecules of water per grammolecule of fluoride is used as a base.

4. A method as claimed in claim 1, characterized in that a freeze-dried tetra(hydrocarbyl)ammonium fluoride which comprises less than 2 grammolecules of water per grammolecule of fluoride is used as a base.

5. A method as claimed in claim 1, characterized in that the dehydrobromination reaction is carried out in an aprotic solvent, at a reaction temperature between −10° C. and 120° C.

6. A method as claimed in claim 5, characterized in that the dehydrobromination reaction is carried out in a solvent selected from the group consisting of tetrahydrofuran, toluene, dimethyl formamide, acetone, a mixture of two of these solvents and a mixture of one of these solvents with an alkane having from 6 to 8 carbon atoms.

7. A method as claimed in claim 6, characterized in that the dehydrobromination reaction is carried out in tetrahydrofuran or in a mixture of tetrahydrofuran and hexane or heptane as a solvent.

8. A method as claimed in claim 7, characterized in that the dehydrobromination reaction is carried out in tetrahydrofuran or in a mixture of tetrahydrofuran and hexane or heptane as a solvent at a reaction temperature between 20° C. and 70° C., preferably at approximately 25° C.

9. A method as claimed in claim 1, characterized in that the starting-material used for the dehydrobromination reaction is a pure 7α-bromo-Δ5-steroid or a mixture of 7α- and 7β-bromo-Δ5-steroid, wherein the α-epimer is present for at least 85%.

10. A method as claimed in claim 9, characterized in that the starting-material used for the dehydrobromination reaction is a mixture of 7α- and 7β-bromo-Δ5-steroids previously equilibrated under the influence of a small quantity of bromide ions until the α-epimer is present in the mixture for at least 85%.

11. A method as claimed in claim 10, characterized in that the equilibration is carried out by leaving the mixture of epimers to stand in an aprotic solvent at a temperature between approximately 0° and 30° C. for at least 30 minutes in the presence of 0.1 to 5 mole%, preferably approximately 1 mole%, of bromide calculated on the mixture of epimers.

12. A method as claimed in claim 11, characterized in that the equilibration is carried out by leaving the mixture of epimers to stand at a temperature between approximately 0° and 30° C. in the presence of a small quantity of an alkali metal bromide, an alkaline earth metal bromide or an ammonium bromide, preferably a tetraalkyl ammonium bromide, in a solvent selected from the group consisting of tetrahydrofuran, toluene, dimethylformamide, acetone, a mixture of two of these solvents and a mixture of one of these solvents with an alkane having from 6 to 8 carbon atoms.

13. The method according to claim 1, wherein said $C_2$-$C_5$ alkanoyl group is ketalized with a $C_1$-$C_4$ alkanol.

14. The method according to claim 1, wherein said $C_1$-$C_{10}$ aliphatic hydrocarbyl group is branched.

15. The method according to claim 1, wherein said $C_1$-$C_{10}$ aliphatic hydrocarbyl group is non-branched.

16. The method according to claim 1, wherein said $C_1$-$C_{10}$ aliphatic hydrocarbyl group is saturated.

17. The method according to claim 1, wherein said $C_1$-$C_{10}$ aliphatic hydrocarbyl group is unsaturated.

18. The method according to claim 1, wherein said $C_1$-$C_{10}$ aliphatic hydrocarbyl group is substituted with at least one fluorine atom.

19. The method according to claim 1, wherein said $C_1$-$C_{10}$ aliphatic hydrocarbyl group is substituted with at least one hydroxy group.

20. The method according to claim 19, wherein said hydroxy group is etherified with at least one $C_1$-$C_4$ alkanol.

21. The method according to claim 19, wherein said hydroxy group is esterified with at least one $C_1$-$C_4$ alkane carboxylic acid.

22. The method according to claim 1, wherein said $R^1$, $R^2$ and $R^3$ are selected from hydroxy groups etherified with $C_1$-$C_4$ alkanols.

23. The method according to claim 1, wherein said $R^1$, $R^2$ and $R^3$ are equal or different and are selected from hydroxy groups esterified with $C_1$-$C_4$ alkane carboxylic acids.

24. The method according to claim 1, wherein said $R^1$, $R^2$ and $R^3$ are equal or different and are selected from hydroxy groups esterified with benzoic acid.

25. The method according to claim 1, wherein said $R^1$ and $R^2$ together consist of a $C_2$-$C_4$ alkylene dioxy group.

* * * * *